(12) United States Patent
Ball

(10) Patent No.: US 8,777,905 B2
(45) Date of Patent: Jul. 15, 2014

(54) LINE STABILIZER FOR INFANTS AND SMALL CHILDREN AND RELATED METHODS

(76) Inventor: Alma Mynon Ball, Dickinson, TX (US)

( * ) Notice: Subject to any disclaimer, the term of this patent is extended or adjusted under 35 U.S.C. 154(b) by 261 days.

(21) Appl. No.: 12/890,708

(22) Filed: Sep. 26, 2010

(65) Prior Publication Data

US 2012/0078193 A1    Mar. 29, 2012

(51) Int. Cl.
*A61M 5/32* (2006.01)
(52) U.S. Cl.
USPC ............................ 604/180; 604/179
(58) Field of Classification Search
USPC ................. 604/174–180
See application file for complete search history.

(56) References Cited

U.S. PATENT DOCUMENTS

| 5,292,312 A * | 3/1994 | Delk et al. ............... 604/180 |
| 5,577,516 A * | 11/1996 | Schaeffer ............... 128/877 |
| 2003/0055382 A1* | 3/2003 | Schaeffer ............... 604/179 |

* cited by examiner

*Primary Examiner* — Quynh-Nhu H Vu
*Assistant Examiner* — Brandy S Lee
(74) *Attorney, Agent, or Firm* — John K. Buche; Buche & Associates, P.C.

(57) ABSTRACT

A preferred system includes a clear medical dressing, a patch with a plurality of hooks, and a strap with a central aperture. A preferable method for I.V. catheter and tubing stabilization comprises the steps of: adhering the patch to the clear dressing; anchoring I.V. tubing to the strap; and contacting the strap to the hooks of the patch so that all of the hooks are covered by the strap and so that a hook and loop connection is established between the hooks of the patch and the material of the strap.

2 Claims, 7 Drawing Sheets

LINE STABILIZER FOR INFANTS AND SMALL CHILDREN AND RELATED METHODS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of Invention

The present invention is in the field of apparatus, systems, and methods for intravenous line stabilization.

2. Background of the Invention

Intravenous ("I.V.") therapy is the introduction of medication to within a blood vessel so that said medication may be delivered throughout a vascular system. Frequently, access to blood vessels for I.V. therapy in humans and other animals is accomplished via the passing of a catheter through a patient's skin until the catheter's cannula is sufficiently within the target vessel. An installed catheter is usually dressed in bandaging since the catheter is partially subcutaneous and within a vessel. Sometimes, medication is delivered during I.V. therapy through tubing connected to a vessel accessing catheter.

I.V. therapy performed using a vessel accessing catheter and tubing can be problematic. One problem with catheter-plus-tubing I.V. therapy is that the tubing is frequently impacted by forces that are capable of dislodging an installed catheter from a preferable vessel accessing position. Dislodged catheters are undesirable since the I.V. therapy may be interrupted, the catheter may need reinstallation which can be painful and/or can introduce infection into the vessel, and the catheter may need to be re-dressed with bandaging which exposes the catheter entry to pathogens. Said dislodgement can be particularly problematic for I.V therapy in infants and small children due to: (1) their constant restlessness and shiftiness which cause additional dislodging forces to effect the I.V. tubing; and, (2) susceptibility to infection. Accordingly, there is a need for systems and methods of I.V. catheter and tubing stabilization that are particularly adapted for use in infant I.V. therapy.

Various systems of I.V. catheter and tubing stabilization are known. For example: U.S. Pat. No. 3,630,195 (issued Dec. 28, 1971) discloses tape that is anchorable to I.V. tubing and wherein the tape may adhere to an I.V. therapy patient's limb away from the catheter installation; U.S. Pat. No. 3,812,851 (issued May 28, 1974) discloses an arm brace for substantially immobilizing an I.V. patient's elbow and for anchoring I.V. tubing to the brace at a location away from a catheter that is positioned adjacent to the braced elbow; U.S. Pat. No. 4,449,975 (issued May 22, 1984), U.S. Pat. No. 4,453,933 (issued Jun. 12, 1984), U.S. Pat. No. 4,591,356 (issued May 27, 1986), and U.S. Pat. No. 7,022,111 (issued Apr. 4, 2006) disclose armbands that are anchorable to tubing and wherein the band may be positioned around an arm away from a catheter installed in the banded arm; U.S. Pat. No. 4,862,904 (issued Sep. 5, 1989) and U.S. Pat. No. 7,406,967 (issued Aug. 5, 2008) discloses arm supports for partially immobilizing the wrist of an I.V. patient so that an I.V. catheter installed at the back of the patient's hand cannot be impacted by forces caused by the arm and wherein the arm support may be anchorable to the tubing; and, U.S. Pat. No. 4,898,587 (issued Feb. 6, 1990) discloses an adhesive sided plate that affixes to a catheter for anchoring, via the adhesive, the catheter to an I.V. patient at the catheter installment site and wherein the associated tubing may be taped to the patient. The above referenced examples are typical of the known stabilization systems.

Although the known systems provide a measure of stabilization to installed I.V. catheters and tubing, the known systems have not been completely adequate for stabilizing I.V. catheters and tubing installed on infant I.V. therapy patients. Specific inadequacies of known I.V. catheter and tube stabilization systems are known. First, braces or support type anchors are only adapted for stabilizing I.V. therapy catheters installed on a particular extremity of the I.V. therapy patient. Second, armband type stabilization systems have a tendency to slide relative to the limb to which the band is placed around whenever the band is impacted by forces (for instance, forces caused by a banded baby rolling or moving within its crib), which sliding dislodges an installed catheter. Also, band anchors must be discomfortably constricted around the limb. Third, tape or adhesive type stabilization systems irritate a baby's sensitive skin; they loose adhesion when wetted or exposed to human excretions; they only cover a small surface area whereby the anchoring function is diminished; and are difficult and painful to relocate when the positioning of the tubing must be changed. For these reasons, and others, there remains a need for systems and methods of I.V. catheter and tubing stabilization that are particularly adapted for use in infant I.V. therapy.

Although not specifically directed to I.V. catheter and tube stabilization, those in medical industries know ways of anchoring medical apparatus to a human body. For instance, U.S. Pat. No. 5,545,191 (issued Aug. 13, 1996) and U.S. Pat. No. 5,843,025 (issued Dec. 1, 1998) disclose adhering a hook patch to the human body and a corresponding loop patch to a medical apparatus (e.g., a hearing aid for U.S. Pat. No. 5,545,191 and a bandage for U.S. Pat. No. 5,843,025) so that the hooks and loops on the patches may form a hook and loop connection when the patches are contacted to one another. These Velcro® type stabilizations suffer from the drawbacks disclosed above in connection with adhesive type stabilization systems. Furthermore, hooks are abrasive and can harm sensitive skin (e.g., a Velcro® patch on a baby's arm may scratch the baby's torso whenever the baby moves). Accordingly, a need still exists for systems and methods of I.V. catheter and tubing stabilization that are particularly adapted for use in infant I.V. therapy.

In non medical industries, systems are known for stabilizing the distal end of a cable to a bundle of the cable. These systems are typically straps that anchor to the distal end and wrap around the corresponding bundle. See U.S. Pat. No. 3,197,830 (issued Aug. 3, 1965), U.S. Pat. No. 5,745,958 (issued May 5, 1998), U.S. Pat. No. 5,802,676 (issued Sep. 8, 1998), U.S. Pat. No. 6,192,554 (issued Feb. 27, 2001), and U.S. Pat. No. D530,600 (issued Oct. 24, 2006). These strap type stabilization means, although not directed to securing a tube to an I.V. therapy patient, would have similar drawback to those mentioned above in connection with band type I.V. stabilization systems and/or Velcro® systems if such were employed to stabilize an I.V. tube. Thus, known stabilization systems do not meet the need for systems and methods of I.V. catheter and tubing stabilization that are particularly adapted for use in infant I.V. therapy.

SUMMARY OF THE INVENTION

It is an object of the present application to disclose apparatus, systems, and related methods for I.V. catheter and tubing stabilization that are particularly adapted for use in infant I.V. therapy. A preferable system includes a clear medical dressing, a patch with a plurality of hooks, and a strap with a central aperture. A preferable method for I.V. catheter and tubing stabilization comprises the steps of: applying the clear medical dressing to the I.V. therapy patient; adhering the patch to the clear dressing; anchoring I.V. tubing to the strap; and, contacting the strap to the hooks of the patch so that all of the hooks are covered by the strap and so that a hook and loop connection is established between the hooks of the patch and the material of the strap.

It is yet another object of the present application to meet the aforementioned needs without any of the drawbacks associated with apparatus heretofore known for the same purpose. It is yet still a further objective to meet these needs in an efficient and inexpensive manner.

BRIEF DESCRIPTION OF THE FIGURES

The manner in which these objectives and other desirable characteristics can be obtained is better explained in the following description and attached figures in which.

It is to be noted, however, that the appended figures illustrate only typical embodiments disclosed in this application, and therefore, are not to be considered limiting of its scope, for the invention may admit to other equally effective embodiments that will be appreciated by those reasonably skilled in the relevant arts. Also, figures are not necessarily made to scale.

DETAILED DESCRIPTION OF PREFERRED EMBODIMENTS

In general, this specification discloses apparatus, systems, and related methods of I.V. catheter and tubing stabilization that are particularly adapted for use in infant I.V. therapy. A preferable system comprises at least one dressing, a plurality of hooks, and at least one strap. Operably, the dressing is preferably applied to an infant I.V. therapy patient; the plurality of hooks may suitably be adhered to the dressing; and the strap may preferably be anchored to I.V. tubing prior to forming a hook-and-loop connection between the hooks and the strap's component material. The more specific features of the disclosed preferable systems and related methods of I.V. catheter and tubing stabilization are best disclosed while referring to the figures.

Figure 1:
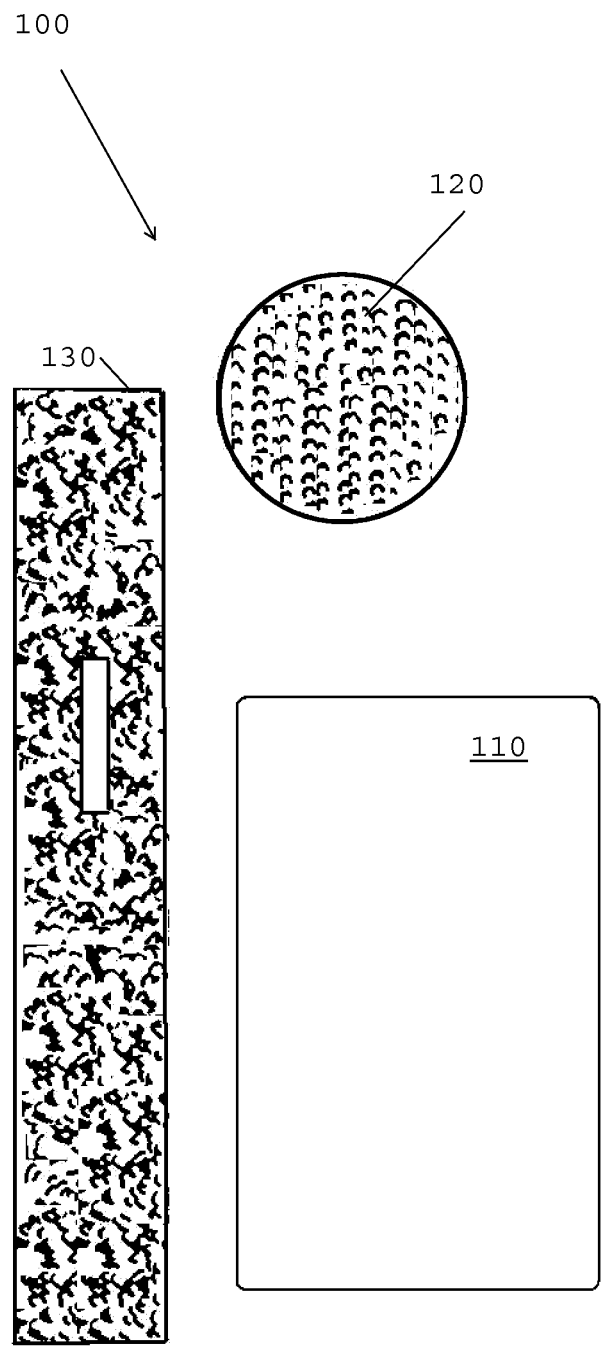
FIG. 1 depicts a preferable disassembled embodiment of the disclosed system 100, including a dressing 110, at least one hook 120, and a strap 130.
Figure 2:
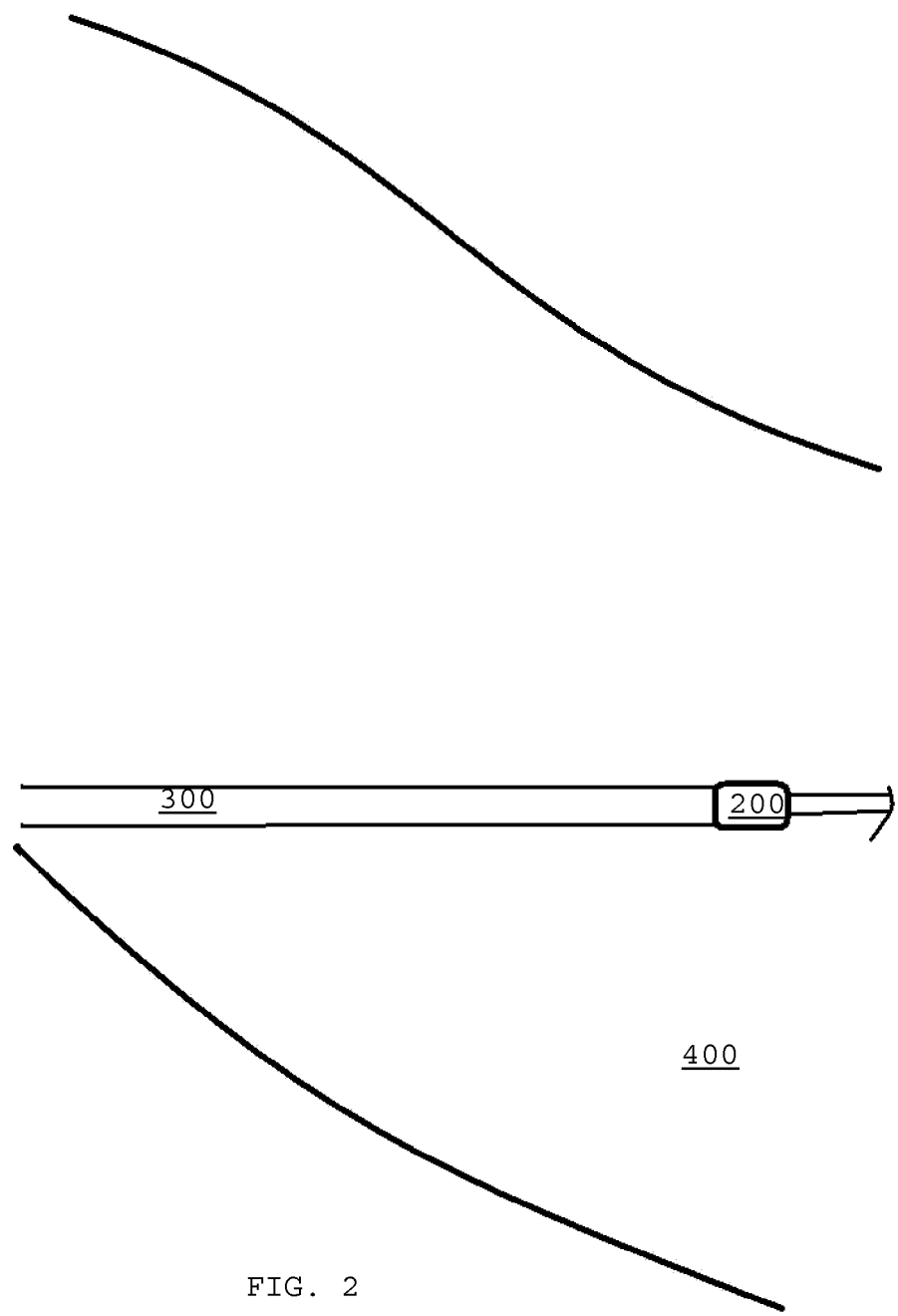
FIG. 2 depicts a patient 400 with an installed catheter 200 and tubing 300.
Figure 6:
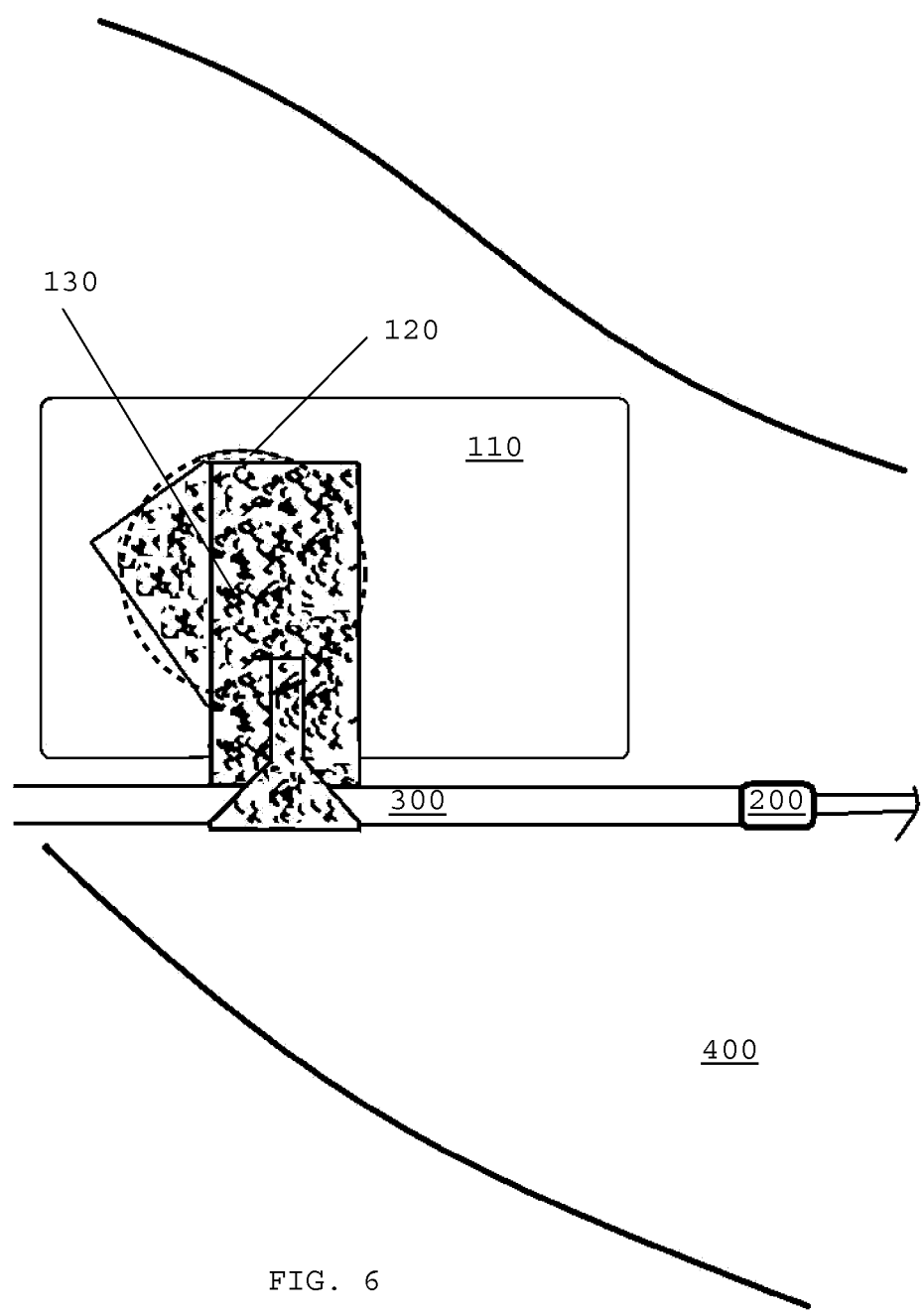
FIG. 6 depicts a preferable embodiment of the disclosed system 100.
Figure 7:
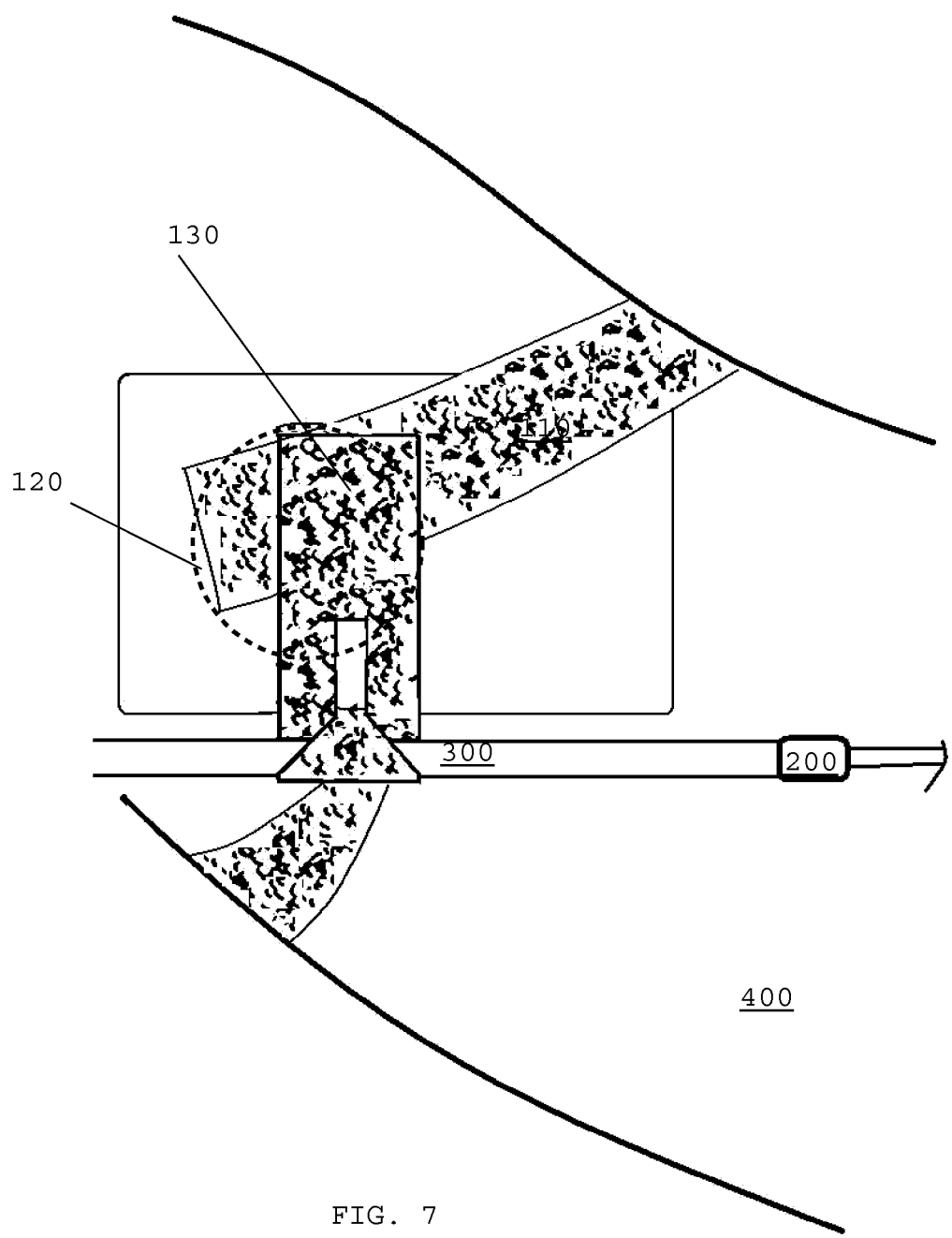
FIG. 7 depicts another preferable embodiment of the disclosed system 100.

FIG. 1 depicts the unassembled components of a disclosed system 100. FIGS. 2 through 5 depict various stages of the assembly of the system 100. FIGS. 6 and 7 depict two preferable embodiments of the assembled system 100 being used for stabilizing an I.V. therapy patient's 400 catheter 200 and associated tubing 300. As depicted in the recited figures, the system comprises at least one dressing 110, a plurality of hooks 120, and at least one strap 130.

Figure 3:
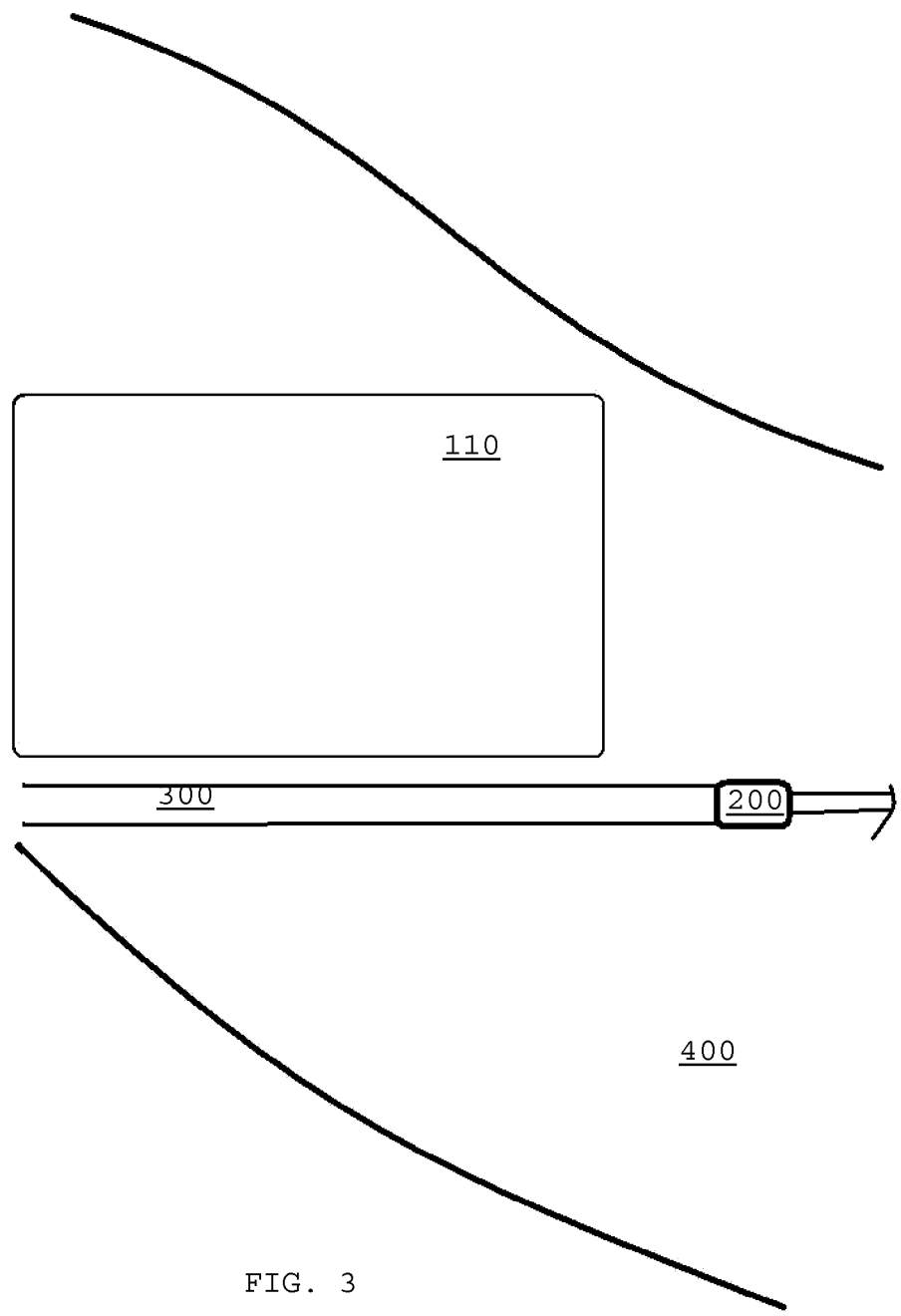
FIG. 3 depicts a patient 400 with an installed catheter 200, tubing 300, and dressing 110.

The dressing 110 is best disclosed with reference to FIGS. 1 and 3. Referring to the stated figures, the dressing 110 may be applied to the patient 400 in any manner known to those of skill in the dressing arts. Suitably the dressing 110 is thin and durable and capable of bonding with adhesives. Preferably, the dressing 110 is approximately four and four-tenths centimeters by four and four-tenths centimeters (4.4 cm×4.4 cm) so the dressing correspondingly covers nineteen and thirty-six hundredths square centimeters (19.36 cm^2) of the patient's 400 body. Although the above shapes and dimensions recited are preferable, the shape of the dressing 110 may vary and, for smaller patients, the dimensions may be reduced. Any type of dressing that is safe for use with infants may be used and will be well known to those of skill in the dressing arts, with a preferable dressing 110 being 3M™ Tegaderm™ transparent film dressing (3M™ catalog no. 1622W).

Figure 4:
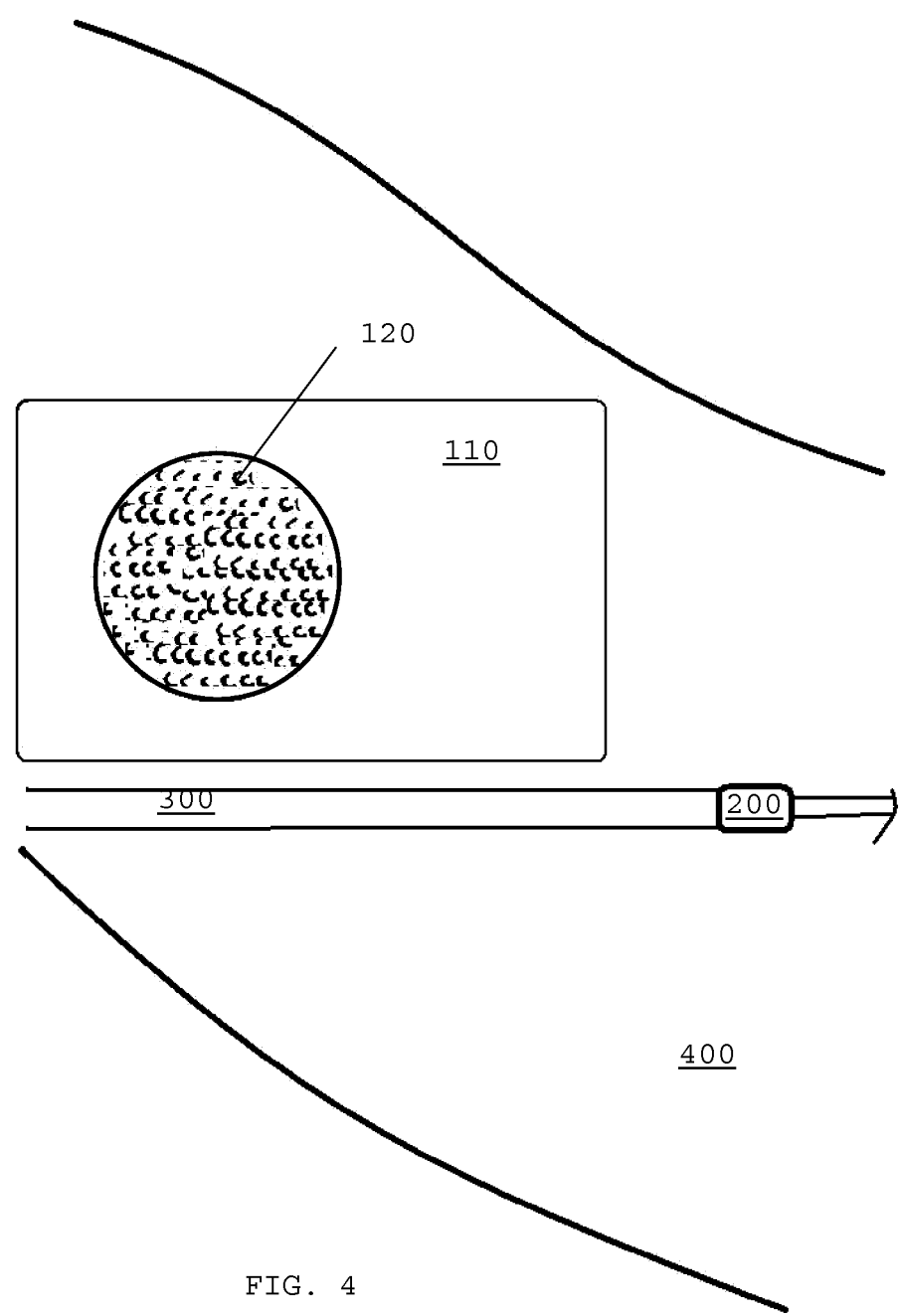
FIG. 4 depicts a patient 400 with an installed catheter 200, tubing 300, and dressing 110 with at least one hook 120.
Figure 5A:
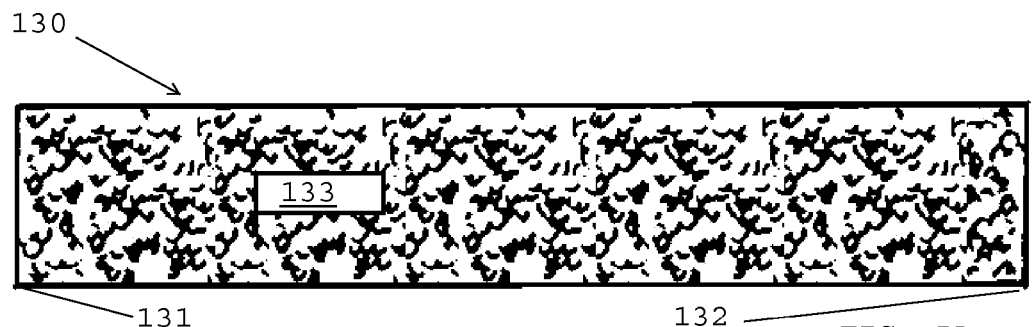
FIG. 5A through 5D depict various stages of a strap 130 being secured to tubing 300.
Figure 5B:
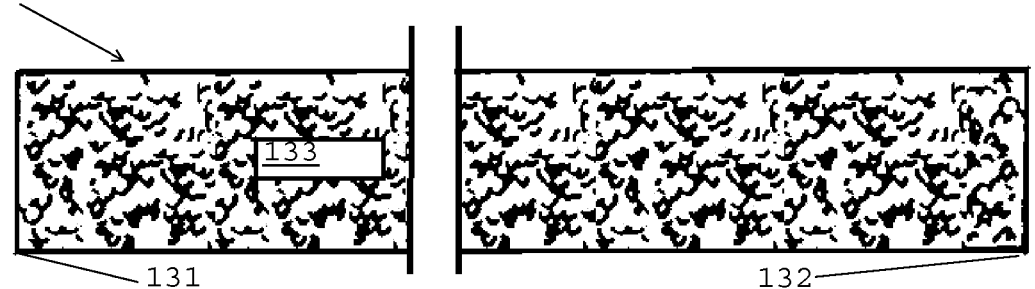
Figure 5C:
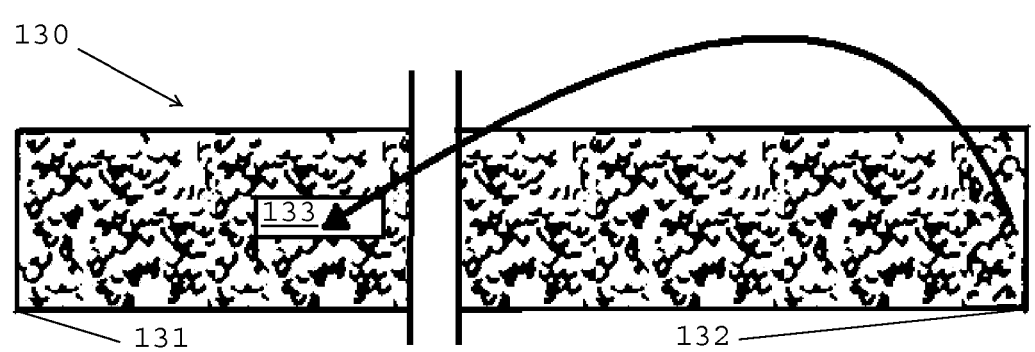
Figure 5D:
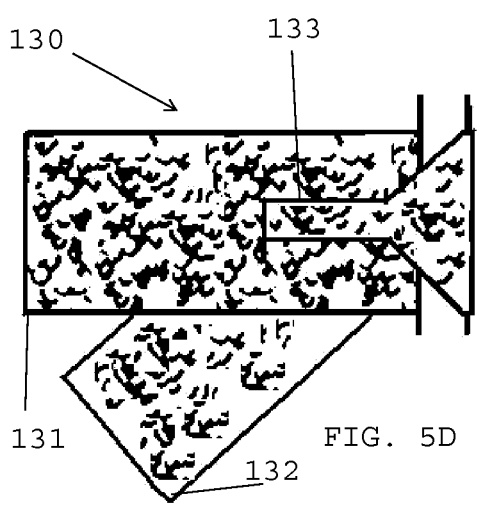

The plurality of hooks 120 are best depicted in FIGS. 1 and 4. As seen in the figures, the plurality of hooks 120 may be adhered to the dressing 110 in any matter known to those of skill in the art of hook and loop fasteners. Preferably, the plurality of hooks 120 should cover a portion of the surface area of the dressing 110, up to and including the entire surface area of the dressing 110. Suitably, the plurality of hooks 120 may be defined by a patch of Velcro® style hooks with an adhesive on its non-hook side. Preferable adhesives will be known or readily apparent to those of skill in the art of Velcro® style patches.

It should be noted that although disclosed and depicted as separate components of the system, the dressing 110 and plurality of hooks 120 need not be constructed as separate units. For example, the hooks 120 may be adhered to the dressing directly rather than being placed on a patch substrate prior to being adhered to the dressing 110.

FIGS. 1 and 5A through 7 suitably depict the strap 130. As shown in the recited figures, the strap 130 suitably features a first end 131, a second end 132, and a centrally located slit 133. As depicted in FIGS. 6 and 7, the strap 130 is configured for anchorage to the I.V. tubing 300 and for securement to the plurality of hooks 120 in the manner of a hook-and-loop fastening system. Referring now to FIGS. 5A through 5D, the configuration for anchorage of the strap 130 to I.V. tubing 300 may preferably be accomplished by the first and second ends 131, 132 and the centrally located slit 133 since, as depicted, the second end 132 may be directed through the slit 133 after the strap has been wrapped around the tubing 300. Referring again to FIGS. 6 and 7, the strap 130 may be anchored at any location along the tubing 200. The configuration for securement to the plurality of hooks 120 may preferably be accomplished by the strap 130 is being comprised of material capable of functioning as the loops of a hook-and-loop fastening system. Acceptable materials will be known or readily apparent to those of skill hook-and-loop connections and may include fabrics comprised of cotton, nylon, polyester, Teflon fibers that form loops. In a preferable embodiment, the strap may be a Velcro® brand fastening strap.

Operably, the disclosed system 100 may be used to stabilize Peripheral Venous Central Lines (PVCLs), Central Venous Lines (CVLs), Chest Tubes, Urinary Catheters, or any tube-like structures entering the body and requiring stabilization. The steps for stabilizing a PVCL, CVL, Chest Tube, or Urinary Catheters (elements 200 and 300 of FIG. 2) to patient 400 according to the disclosed system 100 may be depicted in FIGS. 3 through 6 or 7. First, the dressing 110 is suitably applied to a patient's body 400 distal to the insertion site 300 of the I.V. line 200 as depicted in FIG. 3. Suitably, the shape and size of the dressing may be customized to the patient 400, but it should be noted that the less surface area of the patient covered by the dressing, the less stabilization of the line (element 200 and 300) results. Second, a preferably small patch comprised of at least one hook 120 may be adhered to the dressing 110 as depicted in FIG. 4. Third, the strap may be looped around the I.V. Line (or around the hub of multiple I.V. lines) 200 and the second end 132 thereof directed through the slot 133 as depicted in FIG. 5A through 5D. It should be noted that the strap 130 may be tied to the tube 200 so that the ends 131, and 132 are accessible, but such tying is less preferable. Fourth, the strap 130 ends 131, 132 may be either (1) looped around a portion (e.g., limb, torso, head, neck) of the patient 400 and contacted with the hooks 120 (see FIG. 6) or (2) merely contacted to the hooks 120 (see FIG. 7). It should be noted that the strap ends 131, 132 should cover all of the hooks 120 so that the hooks 120 are not exposed for contact with the patient's body 400.

The disclosed system 100 may be embodied in a kit prior to its installation. Such a kit may be depicted in FIG. 1 and may include a 3M™ Tegaderm™ transparent film dressing 110 (3M™ catalog no. 1622W), a Velcro® style adhesive patch 120, and a Velcro® brand fastening strap 130.

It should be noted that FIGS. 1 through 7 and the associated description are of illustrative importance only. In other words, the depiction and descriptions of the present invention should not be construed as limiting of the subject matter in this application. Additional modifications may become apparent to one skilled in the art after reading this disclosure. For example, the systems 100 disclosed herein are for infants, but it will be understood by those of skill in the art that they may also benefit other patient types.

I claim:

1. A method of stabilizing an I.V. line comprising the steps of:
   identifying an infant I.V. therapy patient with an installed catheter and tubing;
   applying an adhesive backed dressing to the patient at a location that is distal from the catheter installation;
   adhering at least one patch on the dressing;
   locating at least one hook on the patch;
   obtaining a strap with a first end, a second end, and a central slit;
   anchoring the tubing to the strap wherein the strap is wrapped around the tubing;
   introducing the first end of the strap through the central slit;
   contacting the strap to the hook(s) so that a hook-and-loop connection is made between the hooks of the patch and the first end of the strap; and
   wherein contacting the strap to the hook(s) is overlappingly contacting a first end and a second end of the strap to the hook(s).

2. A method of stabilizing an I.V. line comprising the steps of:
   identifying an infant I.V. therapy patient with an installed catheter and tubing;
   applying an adhesive backed dressing to the patient at a location that is distal from the catheter installation;
   adhering at least one patch on the dressing;
   locating at least one hook on the patch;
   obtaining a strap with a first end, a second end, and a central slit;
   anchoring the tubing to the strap wherein the strap is wrapped around the tubing;
   introducing the first end of the strap through the central slit;
   contacting the strap to the hook(s) so that a hook-and-loop connection is made between the hooks of the patch and the first end of the strap; and,
   wherein contacting the strap to the hook(s) is contacting a first end and a second end of the strap to the hook(s);
   wherein the step of contacting the strap to the hook(s) is overlappingly contacting a first end and a second end of the strap to the hook(s) to cover the hook(s) so that the hook(s) is not exposed for contact with the patient.

* * * * *